US010823741B2

(12) United States Patent
Matsumori

(10) Patent No.: US 10,823,741 B2
(45) Date of Patent: Nov. 3, 2020

(54) METHOD FOR DETECTING CARDIAC FAILURE PATIENT

(71) Applicant: Akira Matsumori, Minoh (JP)

(72) Inventor: Akira Matsumori, Minoh (JP)

( * ) Notice: Subject to any disclaimer, the term of this patent is extended or adjusted under 35 U.S.C. 154(b) by 510 days.

(21) Appl. No.: 15/470,336

(22) Filed: Mar. 27, 2017

(65) Prior Publication Data

US 2017/0205428 A1 Jul. 20, 2017

Related U.S. Application Data

(63) Continuation-in-part of application No. PCT/JP2015/078851, filed on Oct. 9, 2015.

(30) Foreign Application Priority Data

Oct. 10, 2014 (JP) ................... 2014-208914

(51) Int. Cl.
*G01N 31/00* (2006.01)
*G01N 33/53* (2006.01)
*G01N 33/68* (2006.01)

(52) U.S. Cl.
CPC ......... *G01N 33/6893* (2013.01); *G01N 33/53* (2013.01); *G01N 33/68* (2013.01); *G01N 2800/325* (2013.01)

(58) Field of Classification Search
None
See application file for complete search history.

(56) References Cited

U.S. PATENT DOCUMENTS

2014/0141986 A1* 5/2014 Spetzler ............... C12Q 1/6886
506/9

FOREIGN PATENT DOCUMENTS

| JP | 2012-502283 A | 1/2012 |
| JP | 2013-18784 A | 1/2013 |
| JP | 2013-526852 A | 6/2013 |
| JP | 2013-545090 A | 12/2013 |
| JP | 2014-505259 A | 2/2014 |
| JP | 2014-512520 A | 5/2014 |

OTHER PUBLICATIONS

MyBioSource (CKAP4 ELISA Kit, Cat #MBS926308 © 2006).*
Rouleau et al. (Stem Cells, 2011, vol. 29, pp. 1672-1683).*
JCS Guidelines 2011 (Circulation Journal, Office Journal of the Japanese Circulation Society, pp. 1-45; http://www.j-circ.or.jp).*
MyBioSource (CKAP4 ELISA Kit, Cat #MBS926308 © 2006) (Year: 2006).*
JCS Guidelines 2011 (Circulation Journal, Office Journal of the Japanese Circulation Society, pp. 1-45; http://www.j-circ.or.jp). Year: 2011).*
Tuffy and Planey (Cell Biology, vol. 2012, Article ID 142313, pp. 1-11). (Year: 2012).*
Chugh et al. Proteomics, Aug. 2013, vol. 13, No. 15, pp. 2324-2334) (Year: 2013).*
Nisha Gupta, et al., "Identification and characterization of p63 (CKAP4/ERGIC-63/CLIMP-63), a surfactant protein A binding protein, on type II pneumocytes", Am J Physiol Lung Cell Mol Physiol., Mar. 26, 2006, pp. L436-L446, vol. 291.
Anja Schweizer, et al., "Characterization of a novel 63 kDa membrane protein Implications for the organization of the ER-to-Golgi pathway", Journal of Cell Science, 1993; pp. 671-683, vol. 104, pt 3.
Andrel V. Nikonov, et al., "Climp-63-mediated binding of microtubules to the ER affects the lateral mobility of translocon complexes", Journal of Cell Science, 2007; pp. 2248-2258, vol. 120, pt 13.
Yoko Shibata, et al., "Mechanisms determining the morphology of the peripheral ER", Cell, 2010, pp. 774-788, vol. 143, No. 5.
Sandra R. Bates, et al., "Role of P63 (CKAP4) in binding of surfactant protein-A to type II pneumocytes", Am J Physiol Lung Cell Mol Physiol, Aug. 15, 2008, pp. L658-L669, vol. 295.
Thomas P. Conrads, et al., "CKAP4/p63 is a Receptor for the Frizzled-8 protein-related Antiproliferative Factor from Interstitial Cystitis Patients", The Journal of Biological Chemistry, Dec. 8, 2006, pp. 37836-37843, vol. 281, No. 49.
Hanief M. Shahjee, et al., "Antiproliferative factor decreases Akt phosphorylation and alters gene expression via CKAP4 in T24 bladder carcinoma cells", Journal of Experimental & Clinical Cancer Research, 2010, 11 pages, vol. 29, No. 160.
Jun Zhang, et al., "Identification of CKAP4/p63 as a Major Substrate of the Palmitoyl Acyltransferase DHHC2, a Putative Tumor Suppressor, Using a Novel Proteomics Method", Molecular & Cellular Proteomics, 2008, pp. 1378-1388, vol. 7.
Shuang-Xi Li, MD., et al., "Prognostic Significance of Cytoskeleton-Associated Membrane Protein 4 and Its Palmitoyl Acyltransferase DHHC2 in Hepatocellular Carcinoma", Cancer, May 15, 2014, pp. 1520-1531, vol. 120., No. 10.
International Search Report for PCT/JP2015/078851 dated Dec. 28, 2015 [PCT/ISA/210].
Communication, dated Jan. 30, 2018, issued by the European Patent Office in counterpart European Application No. 15849135.7.
Communication, dated Mar. 2, 2018, issued by the State Intellectual Property Office of the P.R.C., in counterpart Chinese Application No. 201580052417.5.
Life Science, Inc., "Chemiluminescent Immunoassay Kit for Cytoskeleton Associated Protein 4 (CKAP4), Organism: *Mus musculus* (Mouse) *Instruction manual*," 2011, XP-002777283, URL: http://www.cloud-clone.com/manual/CLIA-Kit-for-Cytoskeleton-Associated-Protein-4--CKAP4--C84577Mu.pdf [retrieved on Jan. 15, 2018], 8 pages.
Written Opinion, dated Jul. 7, 2017, issued by the Singapore Patent Office in counterpart Singapore Patent Application No. 11201702490P.

(Continued)

*Primary Examiner* — Lisa V Cook
(74) *Attorney, Agent, or Firm* — Sughrue Mion, PLLC

(57) ABSTRACT

A method for detecting a cardiac failure patient is provided. The method comprises (1) measuring a value of CKAP4 in a blood sample collected from a subject; (2) comparing the measured value of CKAP4 with a predetermined standard value; and (3) determining the subject as being a cardiac failure patient when the measured value of CKAP4 in the blood sample of the subject is lower than the predetermined standard value.

5 Claims, 8 Drawing Sheets

Specification includes a Sequence Listing.

(56) References Cited

OTHER PUBLICATIONS

Ortega A. et al., Endoplasmic reticulum stress induces different molecular structural alterations in human dilated and ischemic cardiomyopathy. Plos One, Sep. 2014, vol. 9, No. 9, e107635, pp. 1-9 (9 pages).
Zacharias D. A, et al., "Antiproliferative Factor-Induced Changes in Phosphorylation and Palmitoylation of Cytoskeleton-Associated Protein-4 Regulate Its Nuclear Translocation and DNA Binding.", International Journal of Cell Biology, 2012, vol. 2012, pp. 1-13 (14 pages).

* cited by examiner

METHOD FOR DETECTING CARDIAC FAILURE PATIENT

CROSS REFERENCE TO RELATED APPLICATIONS

This application is a Continuation-in-Part of PCT/JP2015/078851, filed Oct. 9, 2015, claiming priority based on Japanese Patent Application No. 2014-208914, filed Oct. 10, 2014.

TECHNICAL FIELD

The present invention relates to a method for detecting a cardiac failure patient.

BACKGROUND ART

Cardiac failure is a clinical syndrome that causes insufficient supply of blood in response to the demand of peripheral organs due to contraction of myocardium and failure of dilation or causes imbalance of blood flow among organs due to contraction of myocardium and failure of dilation. Cardiac failure is caused by underlying diseases such as ischemic cardiac disease (e.g., myocardial infarction) and idiopathic cardiomyopathy (e.g., dilated cardiomyopathy). Diagnosis of cardiac failure is confirmed by screening tests such as medical interview, electrocardiogram examination, and chest X-ray examination, from clinical symptoms such as dyspnea and malaise, and indications at medical examinations. Further, in recent years, supplementary diagnosis of cardiac failure has been performed by measuring brain natriuretic peptide (BNP) or its precursor, i.e., N-terminal pro-brain natriuretic peptide (NT-proBNP).

Cytoskeleton-associated protein 4 (CKAP4) is a type 2 membrane protein (also referred to as p63) having a molecular weight of 63,000 and present in the endoplasmic reticulum (Non-Patent Literatures 1 and 2). Although CKAP4 has been thought to play an important role to keep the structure of the endoplasmic reticulum (Non-Patent Literatures 2 to 4), it has been found that CKAP4 is a receptor on the surface of cells against anti-growth factors, tissue plasminogen activator, surface activated protein A, etc. (Non-Patent Literatures 1, 5 to 7). In addition, it has been reported that CKAP4 inhibits proliferation of bladder cancer cells (Non-Patent Literature 8) and relates to progression and metastasis of hepatocellular carcinoma (Non-Patent Literature 9).

CITATION LIST

Patent Literatures

Non-Patent Literature 1: Gupta N. Manevich Y. Kazi A S. Tao J Q, Fisher A B, Bates S R. Identification and characterization of p63 (CKAP4/ERGIC-63/CLIMP-63), a surfactant protein A binding protein, on type II pneumocytes. Am J Physiol Lung Cell Mol Physiol. 2006; 291: L436-L446.

Non-Patent Literature 2: Schweizer A, Ericsson M, Bachi T. Griffiths G. Hauri H P. Characterization of a novel 63 kDa membrane protein. Implications for the organization of the ER-to-Golgi pathway. J Cell Sci. 1993; 104(pt 3): 671-683.

Non-Patent Literature 3: Nikonov A V, Hauri H P, Lauring B, Kreibich G. Climp-63-mediated binding of microtubules to the ER affects the lateral mobility of translocon complexes. J Cell Sci. 2007; 120(pt 13): 2248-2258.

Non-Patent Literature 4: Shibata Y. Shemesh T, Prinz W A, Palazzo A F, Kozlov M M, Rapoport T A. Mechanisms determining the morphology of the peripheral ER. Cell. 2010; 143: 774-788.

Non-Patent Literature 5: Bates S R, Kazi A S, Tao J Q, et al. Role of P63 (CKAP4) in binding of surfactant protein-A to type II pneumocytes. Am J Physiol Lung Cell Mol Physiol. 2008; 295: L658-L669.

Non-Patent Literature 6: Conrads T P, Tocci G M, Hood B L, et al. CKAP4/p63 is a receptor for the frizzled-8 protein-related antiproliferative factor from interstitial cystitis patients. J Biol Chem. 2006; 281: 37836-37843.

Non-Patent Literature 7: Shahjee H M, Koch K R, Guo L, Zhang C O. Keay S K. Antiproliferative factor decreases Akt phosphorylation and alters gene expression via CKAP4 in T24 bladder carcinoma cells. J Exp Clin Cancer Res. 2010; 29: 160.

Non-Patent Literature 8: Zhang J, Planey S L, Ceballos C. Stevens S M Jr. Keay S K, Zacharias D A. Identification of CKAP4/p63 as a major substrate of the palmitoyl acyltransferase DHHC2, a putative tumor suppressor, using a novel proteomics method. Mol Cell Proteomics. 2008; 7: 1378-1388.

Non-Patent Literature 9: Li S-X. Tang G-S, Zhou D-X et al. Prognostic significance of cytoskeleton-associated membrane protein 4 and its palmitoyl acyltransferase DHHC2 in hepatocellular carcinoma. Cancer 2014; 120: 1520-1531

SUMMARY OF THE INVENTION

Currently, measurement of BNP and NT-proBNP in the blood has been carried out for diagnosis of cardiac failure. However, these markers show high values not only in cardiac failure but also in atrial fibrillation and hypertrophic cardiomyopathy in which cardiac failure has not occurred. Thus, in fact, it is not currently possible to specifically detect cardiac failure patients.

The present invention provides a method for detecting a cardiac failure patient. The method comprises the steps of:

(1) measuring a value of CKAP4 in a blood sample collected from a subject:

(2) comparing the measured value of CKAP4 with a predetermined standard value; and (3) determining the subject as being a cardiac failure patient when the measured value of CKAP4 in the blood sample of the subject is lower than the predetermined standard value.

DESCRIPTION OF EMBODIMENTS

1. Explanation of Terms

Figure 1:
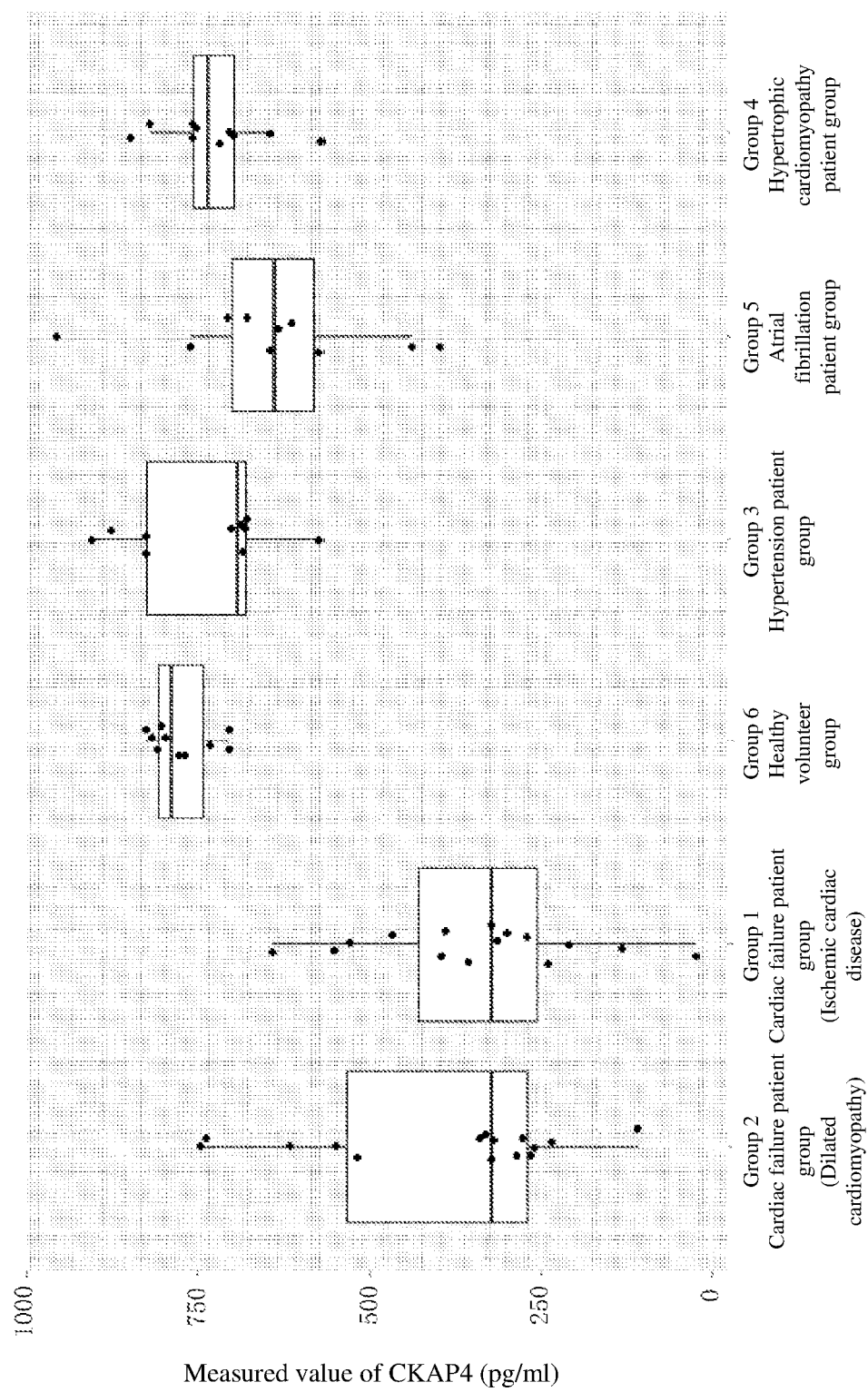
FIG. 1 shows distribution of measured values of CKAP4 when serum of each group is used. The horizontal axis represents each disease group, namely a cardiac failure patient group with dilated cardiomyopathy (group 2), a cardiac failure patient group with ischemic cardiac failure (group 1), a healthy volunteer group (group 6), a hypertension patient group (group 3), an atrial fibrillation patient group (group 5), and a hypertrophic cardiomyopathy patient group (group 4). The vertical axis shows the measured value (pg/ml) of CKAP4.
Figure 2:
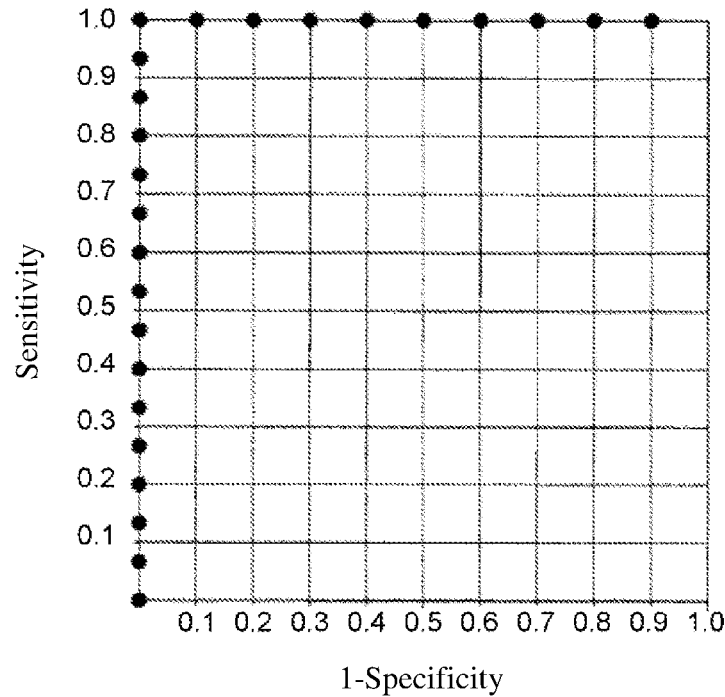
FIG. 2 shows ROC curves of the cardiac failure patient group with ischemic cardiac failure (group 1) and the healthy volunteer group (group 6).
Figure 3:
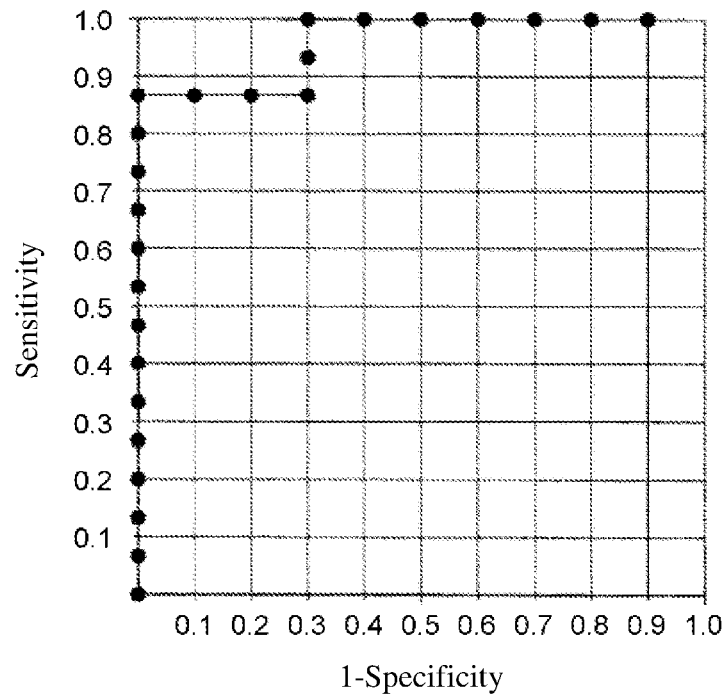
FIG. 3 shows ROC curves of the cardiac failure patient group with dilated cardiomyopathy (group 2) and the healthy volunteer group (group 6).
Figure 4:
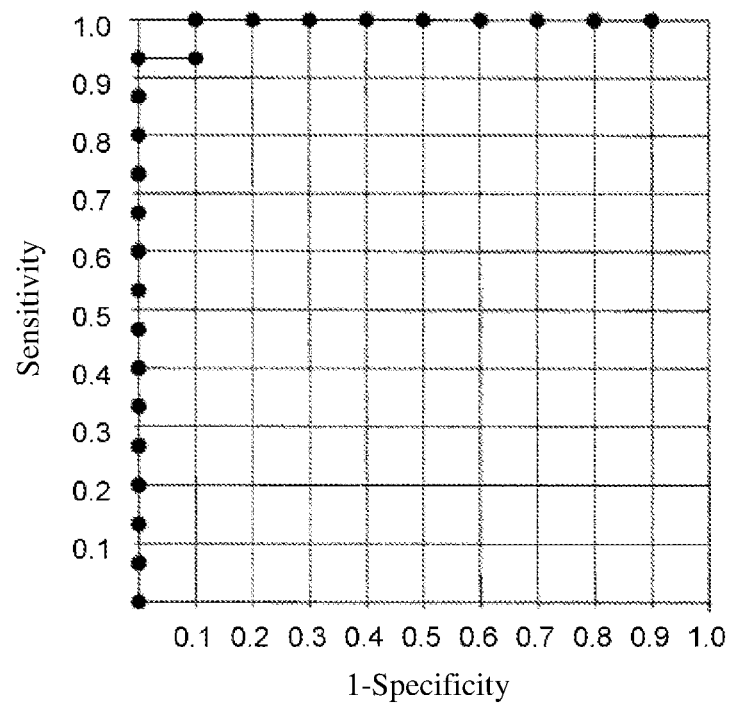
FIG. 4 shows ROC curves of the cardiac failure patient group with ischemic cardiac failure (group 1) and the hypertension patient group (group 3).
Figure 5:
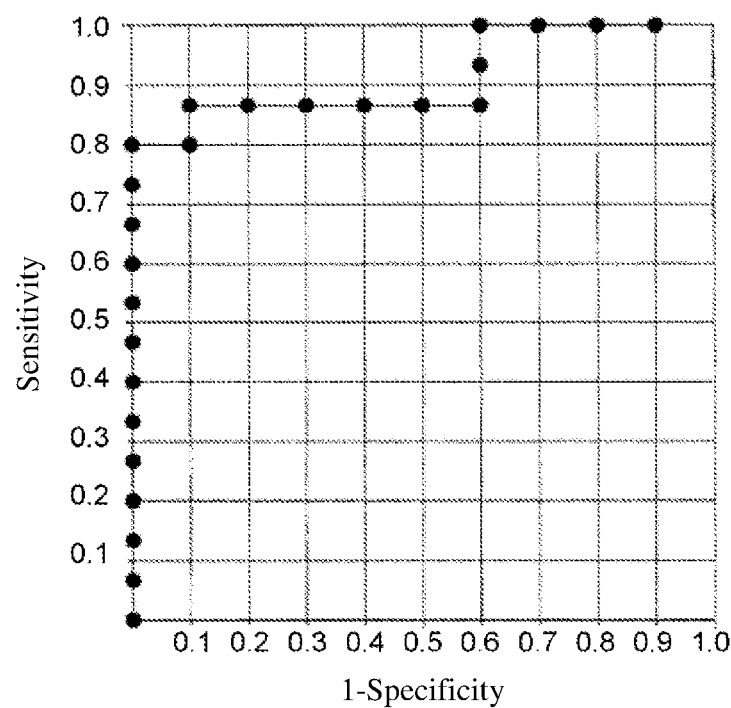
FIG. 5 shows ROC curves of the cardiac failure patient group with dilated cardiomyopathy (group 2) and the hypertension patient group (group 3).
Figure 6:
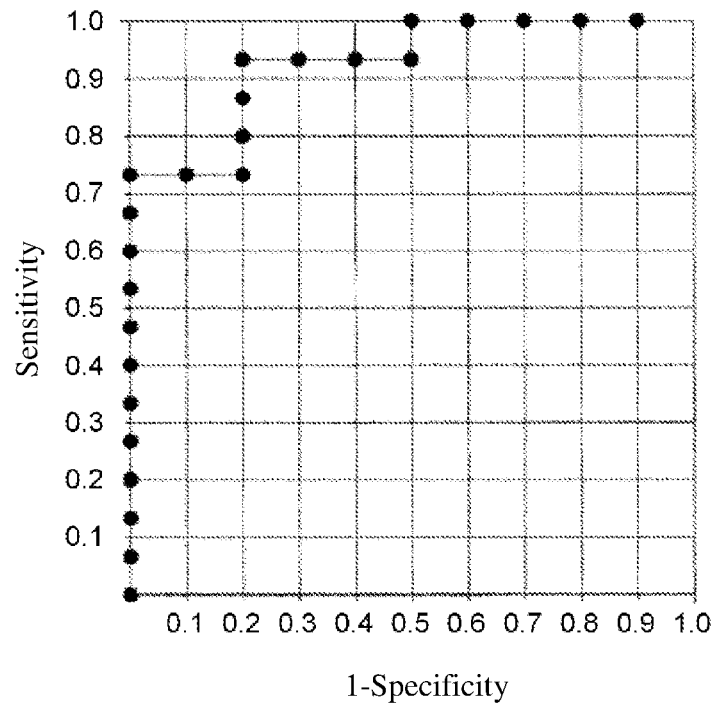
FIG. 6 shows ROC curves of the cardiac failure patient group with ischemic cardiac failure (group 1) and the atrial fibrillation patient group (group 5).
Figure 7:
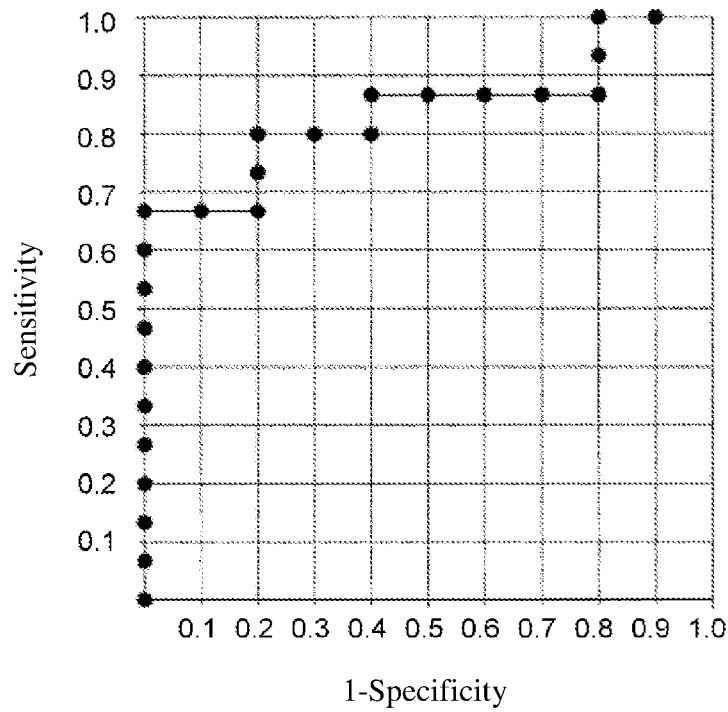
FIG. 7 shows ROC curves of the cardiac failure patient group with dilated cardiomyopathy (group 2) and the atrial fibrillation patient group (group 5).
Figure 8:
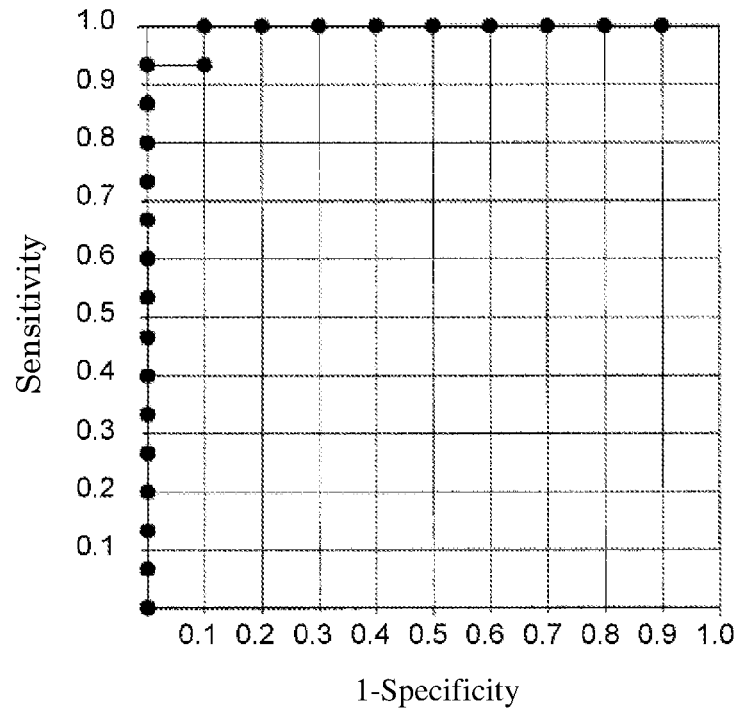
FIG. 8 shows ROC curves of the cardiac failure patient group with ischemic cardiac failure (group 1) and the hypertrophic cardiomyopathy patient group (group 4).
Figure 9:
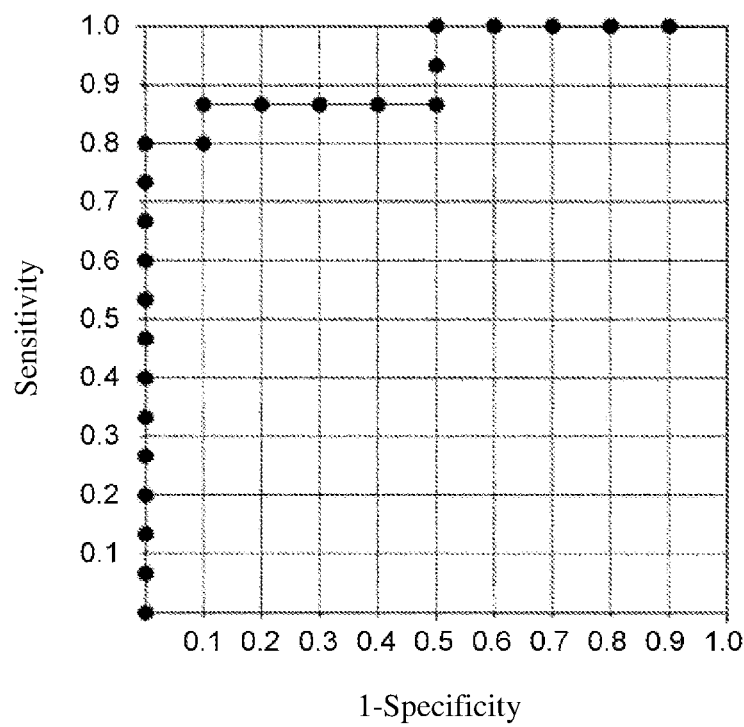
FIG. 9 shows ROC curves of the cardiac failure patient group with dilated cardiomyopathy (group 2) and the hypertrophic cardiomyopathy patient group (group 4).

First, terms used in this specification, claims, and abstract will be described.

"Cardiac failure" is congestive heart failure that can be diagnosed as cardiac failure based on diagnostic criteria for congestive heart failure according to the Framingham study shown in Table 1.

TABLE 1

Diagnosis of cardiac failure requires the simultaneous presence of at least 2 major criteria or 1 major criterion in conjunction with 2 or more minor criteria.

[Major criteria]

Paroxysmal nocturnal dyspnea or orthopnea
Neck vein distention
Pulmonary rales
Increasing heart size
Acute pulmonary edema
Protodiastolic gallop (S3: third heart sound)
Increased venous pressure (16 cm $H_2O$ or more)
Circulation time extension (25 seconds or longer)
Hepatojugular reflux
[Minor criteria]

Lower thigh edema
Nocturnal cough
Exertional dyspnea
Hepatomegaly
Retention of Pleural effusion
Decrease in vital capacity (not more than ⅓ of the maximum volume)
Tachycardia (120/min or more)
[Major criteria and minor criteria]

In the case where the weight loss was 4.5 kg or more in 5 days in response to the therapy, if the weight loss was due to an effect of the therapy of cardiac failure, the case is regarded as one of major symptoms, and if the weight loss was due to an effect of other therapies, the case is regarded as one of small symptoms.

The "cardiac failure" of the present invention includes both acute cardiac failure and chronic cardiac failure. The criteria described in Guidelines for Diagnosis and Treatment of Circulatory Diseases (Report of Joint Study Group of 2010), Guidelines for Cardiac Failure Treatment (revised 2011) (The Japanese Circulation Society, etc.) can be applied as the diagnostic criteria of acute cardiac failure. The criteria described in Guidelines for Diagnosis and Treatment of Circulatory Diseases (Report of Joint Study Group of 2009), Guidelines for Chronic Cardiac Failure Treatment (revised 2010) (The Japanese Circulation Society, etc.) can be applied as the diagnostic criteria of chronic cardiac failure.

Examples of underlying diseases causing cardiac failure include ischemic cardiac diseases such as angina pectoris, acute myocardial infarction, and ischemic cardiomyopathy; cardiomyopathy such as dilated cardiomyopathy, restrictive cardiomyopathy, hypertrophic cardiomyopathy, stress cardiomyopathy, and postpartal cardiomyopathy; hypertension; endocarditis, ruptured chordae tendineae, and valve regurgitation due to aortic dissection; myocarditis; aortic valve stenosis: pericardial diseases such as cardiac tamponade and pericarditis constrictive; congenital cardiac diseases such as atrial septal defect and ventricular septal defect: aortic dissection; valvular diseases such as valve stenosis; pulmonary embolism or pulmonary thrombosis; and high cardiac output syndromes such as sepsis, thyrotoxicosis, anemia, short-circuit disease, beriberi cardiac disease, and Paget's disease. The underlying disease is preferably ischemic cardiac disease, cardiomyopathy, and myocarditis, more preferably ischemic cardiac disease or cardiomyopathy.

"Individual" is not particularly limited, but includes a human and a mammal other than a human. The mammal include bovine, horse, sheep, goat, pig, dog, cat, rabbit, monkey and the like, among which human is preferable. Also, there is no limitation to the age and gender of the individual. Preferably, the individual is a living individual.

"Subject" may be an individual having some diseases or an individual who does not have any disease. The subject may be a person having subjective symptoms such as exertional or non-exertional shortness of breath, dyspnea, orthopnea, malaise, easy fatigue, chest discomfort, chest pain, etc. or may be an asymptomatic person. Further, the subject may include an individual who is suspected of having a cardiac disease according to known diagnostic criteria by medical interview; blood pressure examination; physical examination such as heart sound examination and electrocardiogram examination; chest X-ray examination; chest CT examination; cardiac MR examination; standard 12 induction electrocardiogram examination; echocardiographic examination; biochemical examination of serum or plasma for measuring values of creatinine kinase (CK), aspartate aminotransferase (AST), alanine aminotransferase (ALT), lactate dehydrogenase (LDH), BNP, NT-proBNP, etc.

"Cardiac disease patient" refers to a patient diagnosed as having a cardiac disease according to the known diagnostic criteria described in the description of the "subject". Examples of the cardiac diseases include ischemic cardiac diseases such as angina pectoris, acute myocardial infarction, and ischemic cardiomyopathy; cardiomyopathy such as dilated cardiomyopathy, restrictive cardiomyopathy, hypertrophic cardiomyopathy, stress cardiomyopathy, and postpartal cardiomyopathy; hypertension; arrhythmia such as ventricular tachycardia, ventricular fibrillation, atrial fibrillation, atrial flutter, and supraventricular tachycardia; endocarditis, ruptured chordae tendineae, and valve regurgitation due to aortic dissection; myocarditis; aortic valve stenosis; pericardial diseases such as cardiac tamponade and pericarditis constrictive; congenital cardiac diseases such as atrial septal defect and ventricular septal defect; aortic dissection; valvular diseases such as valve stenosis; pulmonary embolism or pulmonary thrombosis; and high cardiac output syndromes such as sepsis, thyrotoxicosis, anemia, short-circuit disease, beriberi cardiac disease, and Paget's disease. The cardiac disease is preferably ischemic cardiac disease, cardiomyopathy, and myocarditis, more preferably ischemic cardiac disease or cardiomyopathy.

"Blood sample" refers to blood (whole blood) collected from a subject, or serum or plasma prepared from the blood. More preferably, the blood sample is serum or plasma. Even more preferably, the blood sample is serum. The type of anticoagulant used for collecting plasma is not particularly limited. The type of the blood sample of the subject used for measurement and the type of the blood sample used for determining a predetermined standard value may be the same as or different from each other, but are preferably the same as each other. When plasma is used as the blood sample, it is preferable that the plasma for determining the predetermined standard value is prepared from blood collected using the same anticoagulant as in the plasma of the subject. In addition, the blood sample may be a fresh sample or may be a preserved sample. When preserving a blood sample, it can be preserved in a room temperature environment, a refrigerated environment, or a frozen environment, but cryopreservation is preferable.

"Measured value of CKAP4" refers to a value reflecting the amount or concentration of CKAP4 protein (hereinafter simply referred to as "CKAP4"). When the measured value is indicated by "amount", it may be expressed on either a mole basis or a mass basis, but it is preferable to indicate the amount on a mass basis. When the value is expressed in terms of "concentration", it may be a molar concentration or a ratio (mass/volume) of a mass per constant volume of a blood sample, but the value is preferably expressed in terms of a ratio of mass/volume. In addition to the above, the value reflecting the amount or the concentration may be the intensity of a signal such as fluorescence or luminescence.

"Predetermined standard value" refers to a baseline of the measured value of CKAP4. The baseline can be determined based on a measured value of CKAP4 in a blood sample of an individual who does not develop cardiac failure and/or a measured value of CKAP4 in a blood sample of an individual who has developed cardiac failure.

For example, there are obtained CKAP4 measured values measured using blood samples of a plurality of individuals who have developed cardiac failure and CKAP4 measured values measured using blood samples of a plurality of individuals who do not develop cardiac failure. Based on these multiple values, a value that can classify positivity and negativity most accurately can be set as a "baseline". Here, "the value that can classify most accurately" can be appropriately set based on indices such as sensitivity, specificity, positive predictive value, negative predictive value, etc. depending on the purpose of the examination.

For example, as one embodiment, the lowest measured value among measured values of CKAP4 in respective blood samples obtained from a plurality of individuals who do not develop cardiac failure may be used as a baseline. For example, when it is desired to reduce, as in a screening test, the false positive as much as possible, the baseline can be suitably used.

Further, in another embodiment, when determining the baseline based on the measured value of CKAP4 in the blood sample of an individual who has developed cardiac failure, the highest measured value can be determined as the baseline among measured values of CKAP4 in blood samples of a plurality of individuals who have developed cardiac failure. For example, when it is desired to reduce, as in a screening test, the false negative as much as possible, the baseline can be suitably used.

In another embodiment, the baseline is a measured value per se of CKAP4 in a blood sample of an individual who does not develop cardiac failure, or an average value, median value or most frequent value of a plurality of measured values of CKAP4 in individuals who do not develop cardiac failure.

The baseline can also be determined based on measured values of CKAP4 in a plurality of blood samples of individuals who do not develop cardiac failure.

In this case, [the average value of the measured values of CKAP4] in the plurality of blood samples, preferably [a value obtained by subtracting "the value obtained by multiplying the standard deviation value of the measured values of CKAP4 in the plurality of blood samples by 1 from "the average value"], or more preferably [a value obtained by subtracting "the value obtained by multiplying the standard deviation value by 2 from "the average value"] can be used as the baseline.

Furthermore, a measured value of CKAP4 obtained in the past (one measured value may be used, or an average value, median value or most frequent value of a plurality of measured values of CKAP4 may be used) from the same subject before causing cardiac failure, preferably before causing a cardiac disease may be used as the baseline.

When determining the baseline based on the measured value of CKAP4 in the blood sample of the individual who does not develop cardiac failure and the measured value of CKAP4 in the blood sample of the individual who has developed cardiac failure, an average value of a measured value of CKAP4 in a blood sample of one individual who does not develop cardiac failure and a measured value of CKAP4 in a blood sample of one individual who has developed cardiac failure can be used as the baseline. In addition, the "average value of the measured values of CKAP4 in the plurality of blood samples of individuals who do not developed cardiac failure" and the "average value of the measured values of CKAP4 in the plurality of blood samples of individuals who have developed cardiac failure" are further averaged, and the resulting averaged value can be used as the baseline. In other embodiments, an individual who does not develop cardiac failure and an individual who has developed cardiac failure may be grouped, and a median value of measured values of CKAP4 in blood samples of this group may be used as the baseline.

As yet other embodiments, in the method of determining the baseline, a measured value of CKAP4 in a blood sample of a healthy individual may be used instead of the measured value of CKAP4 in the blood sample of the individual who does not develop cardiac failure.

These baselines may be determined when obtaining the measured value of CKAP4 in the blood sample of the subject, but may be determined in advance.

"A measured value of CKAP4 in a blood sample of a subject is lower than the predetermined standard value" or "a measured value of CKAP4 in a blood sample of a cardiac disease patient or a subject suspected of having a cardiac disease is lower than the predetermined standard value" refers to a case where the measured value of CKAP4 in the blood sample of the subject, the cardiac disease patient, or the subject suspected of having a cardiac disease shows a value lower than the predetermined standard value. The lower limit value in this case is not particularly limited, but is preferably "0".

"A measured value of CKAP4 in a blood sample of a cardiac disease patient or a subject suspected of having a cardiac disease is equal to or greater than the predetermined standard value" means that the measured value of CKAP4 in the blood sample of the cardiac disease patient or the subject suspected of having a cardiac disease is equal to or higher than the predetermined standard value. The upper limit value in this case is not particularly limited, but is preferably the highest value that can be shown in the blood sample of the individual.

As still another embodiment, a plurality of baselines may be combined to detect a cardiac failure patient or discriminate a cardiac disease instead of the method of detecting a cardiac failure patient or the method of discrimination of cardiac disease based on the above one baseline. For example, a plurality of measured values of CKAP4 in previously measured cardiac failure patients and individuals who do not have cardiac failure are divided into a plurality of numerical ranges such as "high", "medium", and "low". In this case, when a measured value of CKAP4 in a blood sample of a subject, a cardiac disease patient or a subject suspected of having a cardiac disease is distributed in the numerical range of "low", the individual who provided the blood sample can be determined to have cardiac failure. When a measured value of CKAP4 in a blood sample of a subject, a cardiac disease patient or a subject suspected of having a cardiac disease is distributed in the numerical range of "high", the individual who provided the blood sample can be determined not to have cardiac disease. Furthermore, when a measured value of CKAP4 in a blood sample of a subject, a cardiac disease patient or a subject suspected of having a cardiac disease is distributed in the numerical range of "medium", other examination data and medical findings may be combined to determine the presence or absence of cardiac failure.

"Healthy individual" is not particularly limited, but is preferably a human or a mammal other than a human described in the section "individual", and refers to an individual who does not show abnormal data in examination such as biochemical examination, blood examination, urine examination, serum examination, or physiological examination. The age and gender of the healthy individual are not particularly limited.

"Individual who does not develop cardiac failure" is not particularly limited, but is preferably a human or a mammal other than a human described in the section "individual", and is an individual who cannot be diagnosed as having developed cardiac failure according to known diagnostic criteria.

"A plurality of blood samples" are 2 or more, preferably 5 or more, and more preferably 10 or more blood samples. These may be blood samples taken from different individuals or may be a plurality of blood samples of the same individual collected at different times.

"A plurality of measured values" are 2 or more, preferably 5 or more, and more preferably 10 or more measured values of CKAP4.

"A plurality of individuals" refers to 2 or more individuals, preferably 5 or more individuals, more preferably 10 or more individuals.

The species, age, gender, etc. of a subject are not always necessarily the same as those of an individual from whom a measured value of CKAP4 is obtained in order to determine the baseline, but it is preferable that the species of the subject is the same as that of the individual. In addition, it is preferable that the individual is of the same age and/or gender as the subject.

"Anti-CKAP4 antibody" is not particularly limited as long as the antibody specifically binds to CKAP4, and any of polyclonal antibodies, monoclonal antibodies, and fragments thereof (for example, Fab, F(ab)$_2$, etc.) obtained by immunizing an animal other than a human with CKAP4 or a part thereof as an antigen can be used. Also, immunoglobulin classes and subclasses are not particularly limited.

Preferred examples of CKAP4 used as an antigen and used for preparing an anti-CKAP4 antibody include CKAP4 derived from human (e.g., UniProtKB/Swiss-Prot: Q07065.2), mouse (e.g., NCBI Reference Sequence: NP_780660.1), rat (e.g., CBI Reference Sequence: NP_001102210.1), or the like, and a more preferable example thereof includes human CKAP4 having the amino acid sequence represented by SEQ ID NO: 1. The CKAP4 used as an antigen may be one extracted from mammalian cells by a known method or may be a recombinant protein obtained by recombinant genetic engineering technology. When a part of CKAP4 is used as an antigen, a fragment obtained by digesting CKAP4 with an enzyme or the like may be used as an antigen, or a peptide having the same sequence as the partial amino acid sequence of CKAP4 may be used as an antigen. The peptide can be synthesized by a known method.

Furthermore, as the anti-CKAP4 antibody, for example, a commercially available product such as an anti-human CKAP4 antibody (catalog number: MBS 6009861, etc.) available from MyBioSource Inc. or an anti-CKAP4 antibody (ab84712) reacting with human CKAP4 available from Abcam Corp. (Cambridge, UK) can also be used.

2. Method for Detecting Cardiac Failure Patient

In the present embodiment, a measured value of CKAP4 in a blood sample is obtained, and the measured value of CKAP4 is used to detect a cardiac failure patient.

(i) Step of Obtaining Measured Value of CKAP4

In the present step, first, a measured value of CKAP4 in a blood sample collected from a subject is obtained.

The method of obtaining the measured value of CKAP4 in the blood sample is not particularly limited as long as the measured value of CKAP4 contained in the blood sample can be obtained. In the present step, in order to obtain the measured value of CKAP4, it is possible to use an antibody capable of specifically binding to CKAP4, that is, an anti-CKAP4 antibody. Alternatively, "4. Test Reagent for Cardiac Failure Containing Anti-CKAP4 Antibody" or "5. Test Kit for Cardiac Failure" as will be described later may be used.

The order of mixing a blood sample and an anti-CKAP4 antibody is not particularly limited, and these may be mixed substantially simultaneously or sequentially.

In the present embodiment, it is possible that a complex of the anti-CKAP4 antibody and CKAP4 in the blood sample is first formed and the complex is then immobilized on a solid phase, or the anti-CKAP4 antibody is immobilized on a solid phase in advance and a complex between the immobilized anti-CKAP4 antibody and CKAP4 in the blood sample is formed. More preferred is an embodiment in which the complex is first formed and then the complex is immobilized on a solid phase. Then, the amount or concentration of CKAP4 contained in the blood sample can be measured by detecting the complex immobilized on the solid phase or the complex formed on the solid phase by a method known in the art.

When the complex of the anti-CKAP4 antibody and CKAP4 in the blood sample is first formed and then the complex is immobilized on the solid phase, an anti-CKAP4 antibody modified with biotin or the like is brought into contact with CKAP4 in the blood sample to form the complex. By separately binding avidins to the solid phase beforehand, the complex can be immobilized on the solid phase via binding between biotin and avidins.

When immobilizing the anti-CKAP4 antibody to the solid phase in advance, the mode of immobilization of the anti-CKAP4 antibody to the solid phase is not particularly limited. For example, the anti-CKAP4 antibody may be directly bonded to the solid phase, or the anti-CKAP4 antibody and the solid phase may be indirectly bonded with another substance interposed therebetween. Examples of the direct bond include physical adsorption and the like. Examples of the indirect bond include bonds via a combination of biotin and avidin or streptavidin (hereinafter also referred to as "avidins"). In this case, by preliminarily modifying the anti-CKAP4 antibody with biotin and previously binding the avidins to the solid phase, the anti-CKAP4 antibody and the solid phase can be indirectly bonded via the bond between biotin and avidins. In the present embodiment, it is preferable that the binding between the anti-CKAP4 antibody and the solid phase is an indirect bond via biotin and avidins.

The material of the solid phase is not particularly limited, and for example, it can be selected from organic polymer compounds, inorganic compounds, biopolymers, and the like. Examples of the organic polymer compounds include latex, polystyrene, polypropylene, and the like. Examples of the inorganic compounds include magnetic substances (iron oxide, chromium oxide, ferrite, etc.), silica, alumina, glass, and the like. Examples of the biopolymers include insoluble agarose, insoluble dextran, gelatin, cellulose, and the like. Two or more types of these may be used in combination. The shape of the solid phase is not particularly limited, and examples thereof include particles, membranes, microplates, microtubes, test tubes, and the like. Among them, particles are preferable, and magnetic particles are particularly preferable.

In the present step, B/F separation for removing unreacted free components not forming the complex may be carried out after the formation of the complex, preferably after the formation of the complex and before the detection of a labeling substance. The unreacted free component refers to a component not constituting the complex. Examples of the unreacted free component include an anti-CKAP4 antibody not bonded to CKAP4 and the like. A means for the B/F separation is not particularly limited, but when the solid phase is in the form of particles, the B/F separation can be performed by collecting only a solid phase that has captured the complex by centrifugation. When the solid phase is in the form of container such as a microplate or a microtube, the B/F separation can be performed by removing a liquid containing unreacted free components. Further, in the case where the solid phase is in the form of magnetic particles, the B/F separation can be performed by aspirating and removing a liquid containing unreacted free components by a nozzle in a state where the magnetic particles are magnetically restrained by a magnet. This method is preferable from the viewpoint of automation. After removal of the unreacted free components, the solid phase that has captured the complex may be washed with a suitable aqueous medium such as PBS.

In the present step, the complex can be detected using an anti-CKAP4 antibody labeled with a labeling substance, or using an unlabeled anti-CKAP4 antibody, an anti-immunoglobulin antibody labeled with a labeling substance and capable of binding to the unlabeled anti-CKAP4 antibody, and the like, but it is preferable to use a labeled anti-CKAP4 antibody. It is also preferable that the epitope in the CKAP4 of the labeled anti-CKAP4 antibody is different from the epitope in the CKAP4 of the anti-CKAP4 antibody that binds to the solid phase.

The labeling substance used for the labeled anti-CKAP4 antibody or the labeled anti-immunoglobulin antibody is not particularly limited as long as the labeling substance generates a detectable signal. For example, the labeling substance may be a substance which itself generates a signal (hereinafter, also referred to as "signal generating substance") or a substance which catalyzes the reaction of other substances to generate a signal. Examples of the signal generating substance include a fluorescent substance, a radioactive isotope, and the like. Examples of the substance which catalyzes the reaction of other substances to generate a detectable signal include enzymes. Examples of the enzymes include alkaline phosphatase, peroxidase, 3-galactosidase, luciferase, and the like. Examples of the fluorescent substance include fluorescent dyes such as fluorescein isothiocyanate (FITC), rhodamine, and Alexa Fluor (registered trademark), and fluorescent proteins such as GFP, and the like. Examples of the radioactive isotope include $^{125}$I, $^{14}$C, $^{32}$P, and the like. Among them, as the labeling substance, enzymes are preferable, and alkaline phosphatase is particularly preferable.

The labeled anti-CKAP4 antibody is obtained by labeling an anti-CKAP4 antibody with the above-mentioned labeling substance by a labeling method known in the art. Alternatively, such labeling may be performed using a commercially available labeling kit or the like. As the labeled immunoglobulin antibody, the same method as the labeling of the anti-CKAP4 antibody may be used, or a commercially available product may be used.

In the present step, by detecting a signal generated by the labeling substance of the labeled anti-CKAP4 antibody contained in the complex, the measured value of CKAP4 contained in the blood sample can be obtained. Here, "detecting a signal" includes qualitatively detecting the presence or absence of a signal, quantifying the signal intensity, and semi-quantitatively detecting the signal intensity. Such semi-quantitative detection means to indicate the signal intensity in stages such as "no signal generation", "weak", "medium", and "strong". In the present step, it is preferable to detect the signal intensity quantitatively or semi-quantitatively.

The method per se for detecting a signal is known in the art. In the present step, a measurement method corresponding to the type of signals derived from the above-mentioned labeling substance should be appropriately selected. For example, when the labeling substance is an enzyme, detection of signals may be performed by measuring a signal such as light or color generated by the reaction of the enzyme with a substrate using a known device such as a luminometer or a spectrophotometer.

The substrate of the enzyme can be appropriately selected from known substrates depending on the type of the enzyme. For example, when alkaline phosphatase is used as the enzyme, examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.13,7]decan]-4-yl)phenyl phosphate) and CSPD (registered trademark) (disodium 3-(4-methoxyspiro[1,2-dioxetane-3,2-(5'-chloro)tricyclo[3.3.1.13,7]decan]-4-yl)phenyl phosphate); and chromogenic substrates such as 5-bromo-4-chloro-3-indolyl phosphate (BCIP), disodium 5-bromo-6-chloro-indolyl phosphate, and p-nitrophenyl phosphate. Particularly preferred is CDP-Star (registered trademark). The luminescence of the substrate is preferably detected with a luminometer.

When the labeling substance is a radioactive isotope, a signal, i.e., radiation, can be measured using a known device such as a scintillation counter. When the labeling substance is a fluorescent substance, a signal, i.e., fluorescence, can be measured using a known device such as a fluorescence microplate reader. The excitation wavelength and the fluorescence wavelength can be appropriately determined according to the type of a fluorescent substance used.

The detection results of the signal can be used as the measured value of CKAP4. For example, when quantitatively detecting the signal intensity, the measured value itself of the signal intensity or a value calculated from the measured value can be used as the measured value of CKAP4. Examples of the value calculated from the measured value of the signal intensity include a value obtained by subtracting a measured value of a negative control sample from the measured value; a value obtained by dividing the measured value by a measured value of a positive control sample; a combination thereof; and the like. Examples of the negative control sample include samples not containing CKAP4, such as physiological saline. Examples of the positive control sample include blood samples containing CKAP4 in a predetermined amount or at a predetermined concentration.

Also, in order to obtain the measured value of CKAP4, a commercially available ELISA kit for detecting a protein having the amino acid sequence (SEQ ID NO: 1) of UniProtKB/Swiss-Prot: Q07065.2, such as cytoskeleton-associated protein 4, ELISA Kit (catalog number MBS 926308) of MyBioSource Inc. (San Diego, Calif., USA) can also be used. When the measured value of CKAP4 in the blood sample is obtained using a commercially available kit, such a value can be obtained according to the protocol attached to the kit.

(ii) Step of Comparing Measured Values of CKAP4 and Determining Cardiac Failure Patient Next, the measured value of CKAP4 in the blood sample of the subject obtained in step (i) mentioned above is compared with the predetermined standard value according to a known method such as a simple comparison method or a statistical test.

Then, according to the definition for determining that "a measured value of CKAP4 in a blood sample of a subject is lower than the predetermined standard value" described in the above "1. Explanation of Terms", the subject from whom the blood sample is taken can be determined to be a cardiac failure patient when the measured value of CKAP4 in the blood sample of the subject is lower than the predetermined standard value. The description in the above "1. Explanation of Terms" relating to "Subject". "Blood sample", "Measured value of CKAP4", "Predetermined standard value", etc. can be incorporated herein.

The detection results obtained by the "Method for Detecting Cardiac Failure Patient" of the present invention are provided to a physician or the like to assist diagnosis of cardiac failure by the physician or the like. Confirmation diagnosis of cardiac failure can also be performed by combining other examination data and medical findings with these detection results.

3. Method for Discrimination of Cardiac Disease

The present invention provides a method of obtaining a measured value of CKAP4 in a blood sample and discriminating, based on the measured value of CKAP4, whether or not a cardiac disease patient or a subject suspected of having a cardiac disease is developing cardiac failure.

(i) Step of Obtaining Measured Value of CKAP4

In the discrimination method of the present invention, first, a measured value of CKAP4 in a blood sample collected from a cardiac disease patient or a subject suspected of having a cardiac disease is obtained. As for the method of obtaining the measured value of CKAP4, the method described in the step (i) of the above "2. Method for Detecting Cardiac Failure Patient" can be similarly used, and the description can be incorporated herein.

(ii) Step of Comparing Measured Value of CKAP4 and Step of Discriminating Cardiac Disease Next, the measured value of CKAP4 in the blood sample of the patient or the subject, obtained in the step (i) above, is compared with the predetermined standard value according to a known method such as a simple comparison method or a statistical test.

Then, according to the definition for determining that "a measured value of CKAP4 in a blood sample of a cardiac disease patient or a subject suspected of having a cardiac disease is lower than the predetermined standard value" or "a measured value of CKAP4 in a blood sample of a cardiac disease patient or a subject suspected of having a cardiac disease is equal to or greater than the predetermined standard value" described in "1. Explanation of Terms", the patient or the subject can be determined to be affected with cardiac failure when the measured value of CKAP4 in the blood sample of the cardiac disease patient or the subject suspected of having a cardiac disease is lower than the predetermined standard value, or the patient or the subject can be determined to be affected with a cardiac disease other than cardiac failure when the concentration of CKAP4 in the blood sample of the patient or the subject is equal to or greater than the predetermined standard value. The description in the above "1. Explanation of Terms" related to "Cardiac disease patient", "Subject suspected of having cardiac disease", "Blood sample", "Measured value of CKAP4", "Predetermined standard value", etc. can be incorporated herein.

The discrimination results obtained by the "Method for Discrimination of Cardiac Disease" of the present invention are provided to a physician or the like to assist diagnosis of cardiac failure by the physician or the like. Confirmation diagnosis of cardiac failure can also be performed by combining other examination data and medical findings with these detection results.

4. Test Reagent for Cardiac Failure Containing Anti-CKAP4 Antibody

The present invention provides a test reagent for cardiac failure containing an anti-CKAP4 antibody used in the above "2. Method for Detecting Cardiac Failure Patient" or "3. Method for Discrimination of Cardiac Disease".

As the anti-CKAP4 antibody, those described in the above "1. Explanation of Terms" can be used.

The test reagent of this embodiment should contain at least one type of anti-CKAP4 antibody. In the case where the anti-CKAP4 antibody is a polyclonal antibody, the anti-CKAP4 antibody may be a polyclonal antibody obtained by immunization with one type of antigen, or may be a polyclonal antibody obtained by immunizing the same individual in parallel with two or more types of antigens. Alternatively, each polyclonal antibody obtained by inoculating two or more types of antigens into different animals respectively may be mixed. When the anti-CKAP4 antibody is a monoclonal antibody, the anti-CKAP4 may be a monoclonal antibody produced from one type of hybridoma, but may be a monoclonal antibody produced from two or more types of hybridomas, in which two or more types of a plurality of monoclonal antibodies each recognizing the same or different epitopes may be contained. Alternatively, at least one type of polyclonal antibodies and at least one type of monoclonal antibodies may be contained as a mixture.

The form of the anti-CKAP4 antibody contained in the test reagent is not particularly limited, and the form may be a dry state or liquid state of antiserum or ascites containing the anti-CKAP4 antibody. Alternatively, the form of the anti-CKAP4 antibody may be a dry state or aqueous solution of a purified anti-CKAP4 antibody, an immunoglobulin fraction containing the anti-CKAP4 antibody, or an IgG fraction containing the anti-CKAP4 antibody.

When the form of the anti-CKAP4 antibody is a dry state or liquid state of antiserum or ascites containing the anti-CKAP4 antibody, at least one of stabilizers such as β-mercaptoethanol and DTT: protective agents such as albumin; surfactants such as polyoxyethylene(20) sorbitan mono laurate and polyoxyethylene(10) octylphenyl ether; preservatives such as sodium azide; and the like may be contained. When the form of the anti-CKAP4 antibody is a dry state or aqueous solution of a purified anti-CKAP4 antibody, an immunoglobulin fraction containing the anti-CKAP4 antibody or an IgG fraction containing the anti-CKAP4 antibody, at least one of buffer components such as a phosphate buffer; stabilizers such as β-mercaptoethanol and DTT; protecting agents such as albumin; salts such as sodium chloride; surfactants such as polyoxyethylene(20) sorbitan monolaurate and polyoxyethylene(10) octylphenyl ether; and preservatives such as sodium azide may be further contained.

In the present invention, the anti-CKAP4 antibody may be unlabeled or may be labeled with biotin or the aforementioned labeling substance, but is preferably labeled with biotin or the aforementioned labeling substance. As the labeling substance, those exemplified in the above section of "2. Method for Detecting Cardiac Failure Patient" can be used, but alkaline phosphatase is preferred. Further, in the present invention, the anti-CKAP4 antibody may be provided in a state of being immobilized on a solid phase surface or the like. The solid phase and the immobilization are as exemplified in the above section of "2. Method for Detecting Cardiac Failure Patient". The solid phase is preferably magnetic beads.

5. Test Kit for Cardiac Failure

The present invention provides a test kit for cardiac failure to be used in a detection method for a cardiac failure patient or a discrimination method for a cardiac disease, which includes the above "4. Test Reagent for Cardiac Failure Containing Anti-CKAP4 Antibody".

More specifically, the present invention provides a test kit for cardiac failure, including a test reagent containing an anti-CKAP4 antibody labeled with biotin as well as a test reagent containing an anti-CKAP4 antibody labeled with a labeling substance. The labeling substance is preferably alkaline phosphatase. The present embodiment may further include a solid phase, preferably a solid phase to which avidins are bonded, more preferably magnetic beads to which avidins are bonded. Further, the present embodiment may include a substrate. The substrate is preferably CDP-Star (registered trademark).

The details of the labeling substance, solid phase, and substrate are as described in "2. Method for Detecting Cardiac Failure Patient", and the description can be incorporated herein.

The test kit of the present embodiment preferably contains two types of anti-CKAP4 antibodies (first anti-CKAP4 antibody and second anti-CKAP4 antibody) which bind to different epitopes of CKAP4, respectively. In this case, a complex of the first anti-CKAP4 antibody. CKAP4, second anti-CKAP4 antibody and labeling substance is formed on the solid phase. This detection method is generally called a sandwich ELISA. In this complex, the first anti-CKAP4 antibody is immobilized on the solid phase and the second anti-CKAP4 antibody is directly or indirectly bonded to the labeling substance. Here, the fact that the second anti-CKAP antibody is indirectly bonded to the labeling substance means that the labeling substance is bonded to the second anti-CKAP4 antibody via an antibody or the like. An example of the indirect bonding includes a state in which a labeled antibody recognizing the second anti-CKAP4 antibody is bonded to the second anti-CKAP4 antibody.

In the case where the first anti-CKAP4 antibody is previously bonded to the solid phase, the test kit of the present embodiment may include the solid phase on which the first anti-CKAP4 antibody is immobilized, the second anti-CKAP4 antibody, and the labeling substance. The second anti-CKAP4 antibody and the labeling substance may be contained in separate containers or may be contained in the same container. When the labeling substance is an enzyme and the test kit further includes a substrate, it is necessary that the enzyme and the substrate be contained in separate containers. When the test kit is provided to a user, at least two types of the solid phase, the second anti-CKAP4 antibody, and the labeling substance may be packed together, or they may be separately packed.

In the case where the first anti-CKAP4 antibody is not previously bonded to the solid phase, the test kit of the present embodiment may include the solid phase, the first anti-CKAP4 antibody, the second anti-CKAP4 antibody, and the labeling substance. At least two types of the first anti-CKAP4 antibody, the second anti-CKAP4 antibody, and the labeling substance may be contained in the same container, or they may be contained in separate containers. When the labeling substance is an enzyme and the test kit further contains a substrate, it is necessary that the enzyme and the substrate be contained in separate containers. When the test kit is provided to a user, at least two types of the solid phase, the first anti-CKAP4 antibody, the second anti-CKAP4 antibody, and the labeling substance may be packed together, or they may be separately packed.

Figure 10:
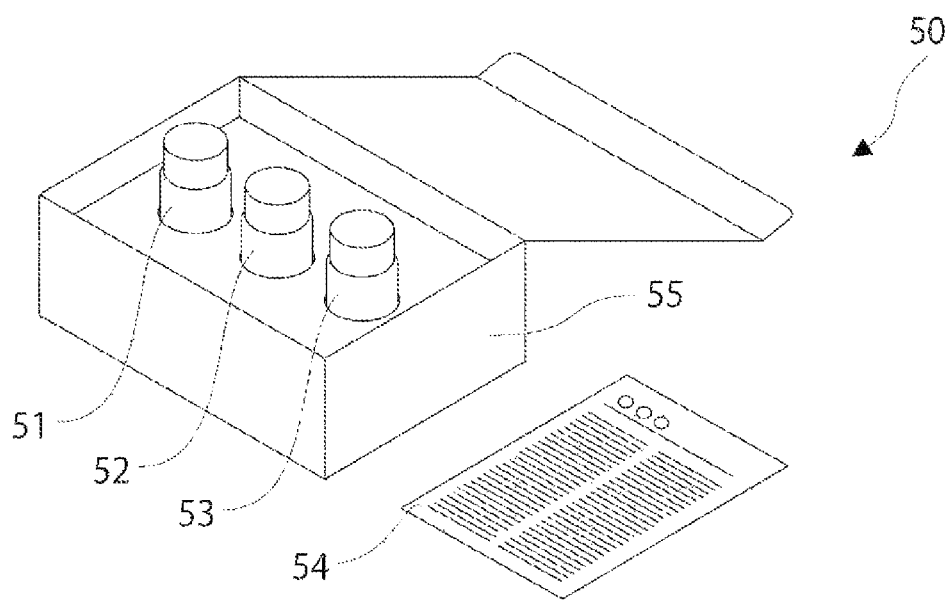
FIG. 10 is a schematic view showing an example of a test kit.

The test kit can be provided to a user as a kit as shown in FIG. 10. A test kit 50 for cardiac failure includes an exterior box 55, a first container 51 containing a plurality of magnetic particles as a solid phase, a second container 52 containing a first anti-CKAP4 antibody capable of binding to the solid phase, a third container 53 containing a second anti-CKAP4 antibody labeled with an enzyme, and a package insert 54 of the test kit. In the package insert 54, the handling method of the test kit, the storage conditions, the expiration date, etc. can be described. In the package insert 54, how to treat a cardiac failure may also be described. How to treat a cardiac failure is described below. A container containing a substrate reagent, a container containing an aqueous medium for washing, and the like may be packed in the exterior box 55.

Figure 11:
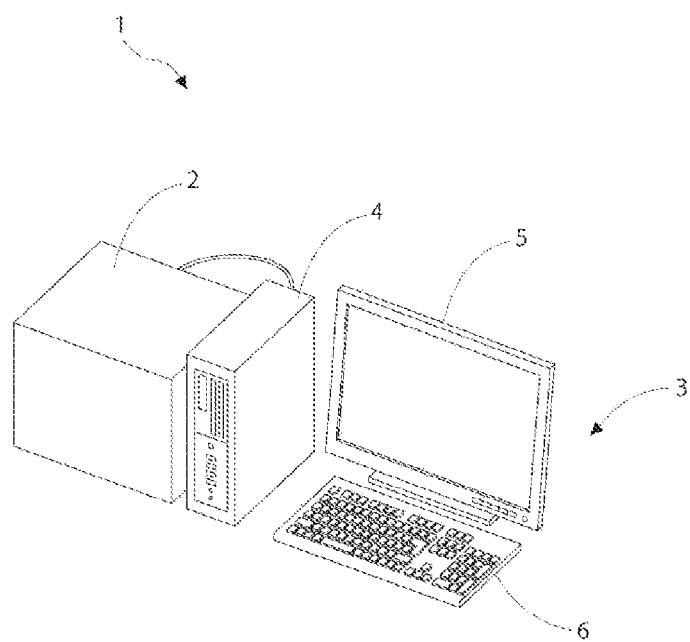
FIG. 11 is a schematic view showing an example of a device for detecting a cardiac failure patient.

6. Detection Device for Cardiac Failure Patient and Detection Program for Cardiac Failure Patient Hereinafter, one embodiment of a detection device and a detection program for implementing the method of the present embodiment will be described with reference to the accompanying drawings. FIG. 11 is a schematic view of a detection device 1. The detection device 1 includes a measuring device 2 and a computer system 3 connected to the measuring device 2.

The measuring device 2 measures a measured value of CKAP4 in a blood sample collected from a subject. The measuring device 2 is not particularly limited, and can be appropriately selected according to the measuring method of CKAP4. The measuring device 2 of the present embodiment is a measuring device capable of detecting a signal generated by an ELISA method using a biotin-labeled anti-CKAP4 antibody, magnetic particles having avidins immobilized thereon, and an anti-CKAP4 antibody labeled with a labeling substance. This type of measuring device is not particularly limited as long as it can detect a signal based on the labeling substance used, and such a measuring device can be appropriately selected according to the type of the labeling substance.

When a biotin-labeled anti-CKAP4 antibody, a test reagent containing magnetic particles having avidins immobilized thereon, a reagent containing an anti-CKAP4 antibody labeled with a labeling substance, and a blood sample collected from a patient are set in the measuring device 2, the measuring device 2 executes an antigen-antibody reaction using each reagent, obtains a signal as optical information based on a labeled antibody specifically bonded to CKAP4, and then transmits the obtained optical information the computer system 3.

The computer system 3 includes a computer 4, an input part 5 for inputting data and the like, and a display part 6 for displaying information on a subject, detection results, and the like. Based on the optical information received from the measuring device 2, the computer system 3 obtains the measured value of CKAP4 in the blood sample collected from the subject, and detects whether or not the subject is a cardiac failure patient based on the measured value of CKAP4. As shown in FIG. 11, the computer system 3 may be an instrument separate from the measuring device 2, or may be incorporated in the measuring device 2.

Figure 12:
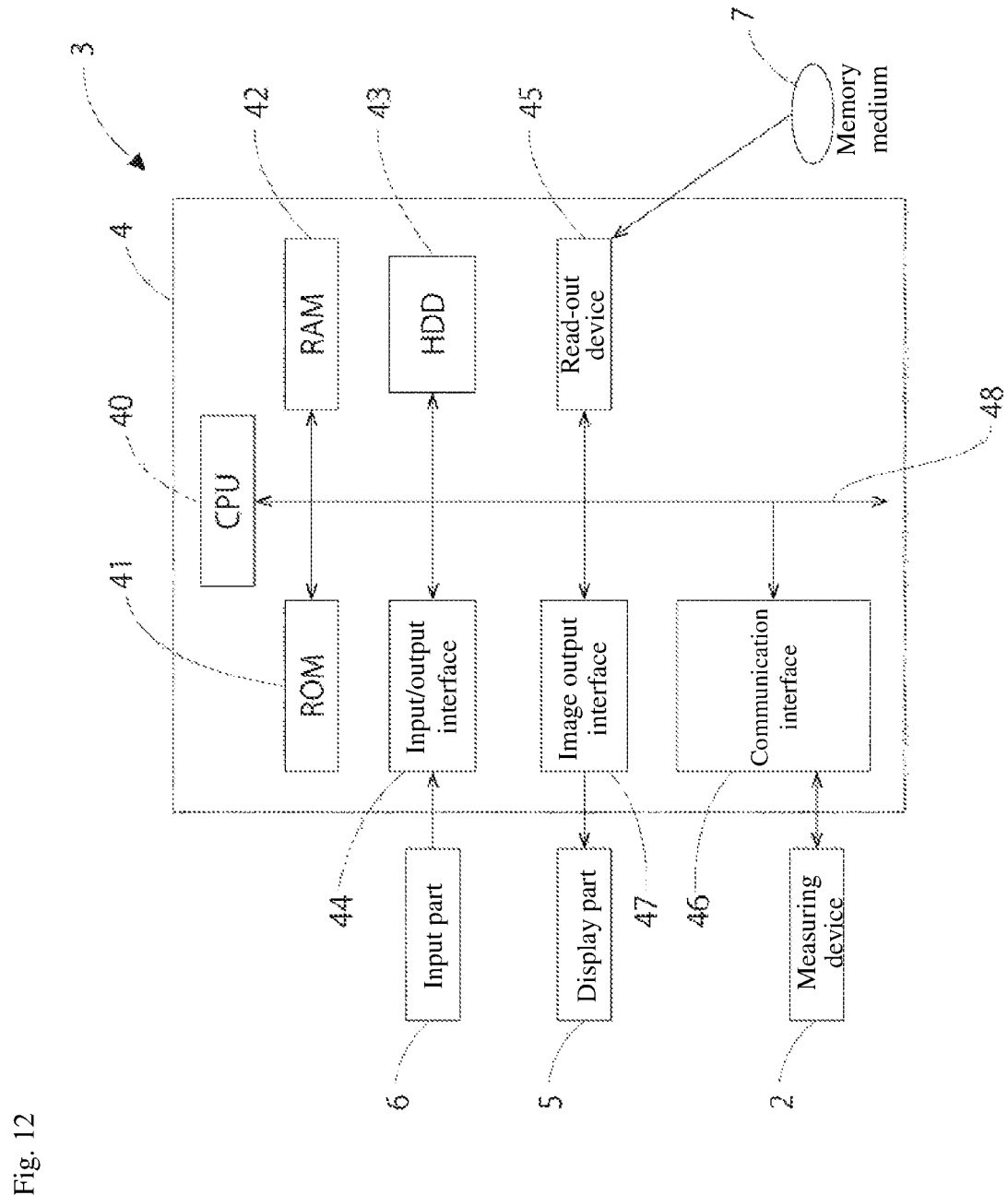
FIG. 12 is a block diagram showing a hardware configuration of the device for detecting a cardiac failure patient.

As shown in FIG. 12, the computer 4 includes a processor (CPU) 40, ROM 41, RAM 42, a hard disk (HDD) 43, an input/output interface 44, a read-out device 45, a communication interface 46, and an image output interface 47, and they are connected via a bus 48 so as to enable data communication. Further, the measuring device 2 is communicably connected to the computer 4 via a communication interface 46.

The CPU 40 controls a series of operations of each input/output part and executes a computer program stored in the ROM 41 or the hard disk 43. That is, the CPU 40 processes the optical information received from the measuring device 2 in accordance with the computer program, calculates the measured value of CKAP4 in the blood sample, and reads out a predetermined standard value (cutoff value) stored in the ROM 41 or in the hard disk 43. When the measured value of CKAP4 is lower than the predetermined standard value, the subject from whom the blood sample is taken is determined to be a cardiac failure patient. Then, the CPU 40 outputs the determination results and displays the results on a display part 5.

The ROM 41 is made up with mask ROM, PROM, EPROM, EEPROM, or the like. As described above, the ROM 41 stores a computer program (cardiac failure patient detection program) for detecting a cardiac failure patient executed by the CPU 40 and data used for executing the cardiac failure patient detection program. The ROM 41 stores, in addition to the predetermined standard value, the measured values of CKAP4 of the subject measured in the past, and the like.

The RAM 42 is made up with SRAM, DRAM, or the like. The RAM 42 is used for reading out the computer program stored in the ROM 41 and the hard disk 43. The RAM 42 is also used as a work area of the CPU 40 when the CPU 40 executes these computer programs.

An operating system to be executed by the CPU 40, computer programs such as application programs (cardiac failure patient detection programs) and data used for executing the computer programs are stored in the hard disk 43. The hard disk 43 stores, in addition to the predetermined standard value (cutoff value), the measured values of CKAP4 of the subject measured in the past, and the like.

The read-out device 45 is made up with a flexible disk drive, a CD-ROM drive, a DVD-ROM drive, or the like. The read-out device 45 can read out the computer program or data stored on a portable memory medium 7.

The input/output interface 44 is made up with, for example, a serial interface such as USB, IEEE 1394, or RS-232C, a parallel interface such as SCSI, IDE, or IEEE 1284, and an analog interface formed by a D/A converter, an A/D converter, or the like. The input/output interface 44 is connected to the input part 5 such as a keyboard or a mouse. A user can input various commands into the computer 3 by means of the input part 5.

The communication interface 46 is, for example, an Ethernet (registered trademark) interface. The computer 3 can transmit print data to a printer or the like through the communication interface 46.

The image output interface 47 is connected to the display part 6 made up with a LCD, a CRT and the like. The display part 6 can output an image signal according to image data provided by the CPU 40. The display part 6 displays an image according to the input image signal.

Figure 13:
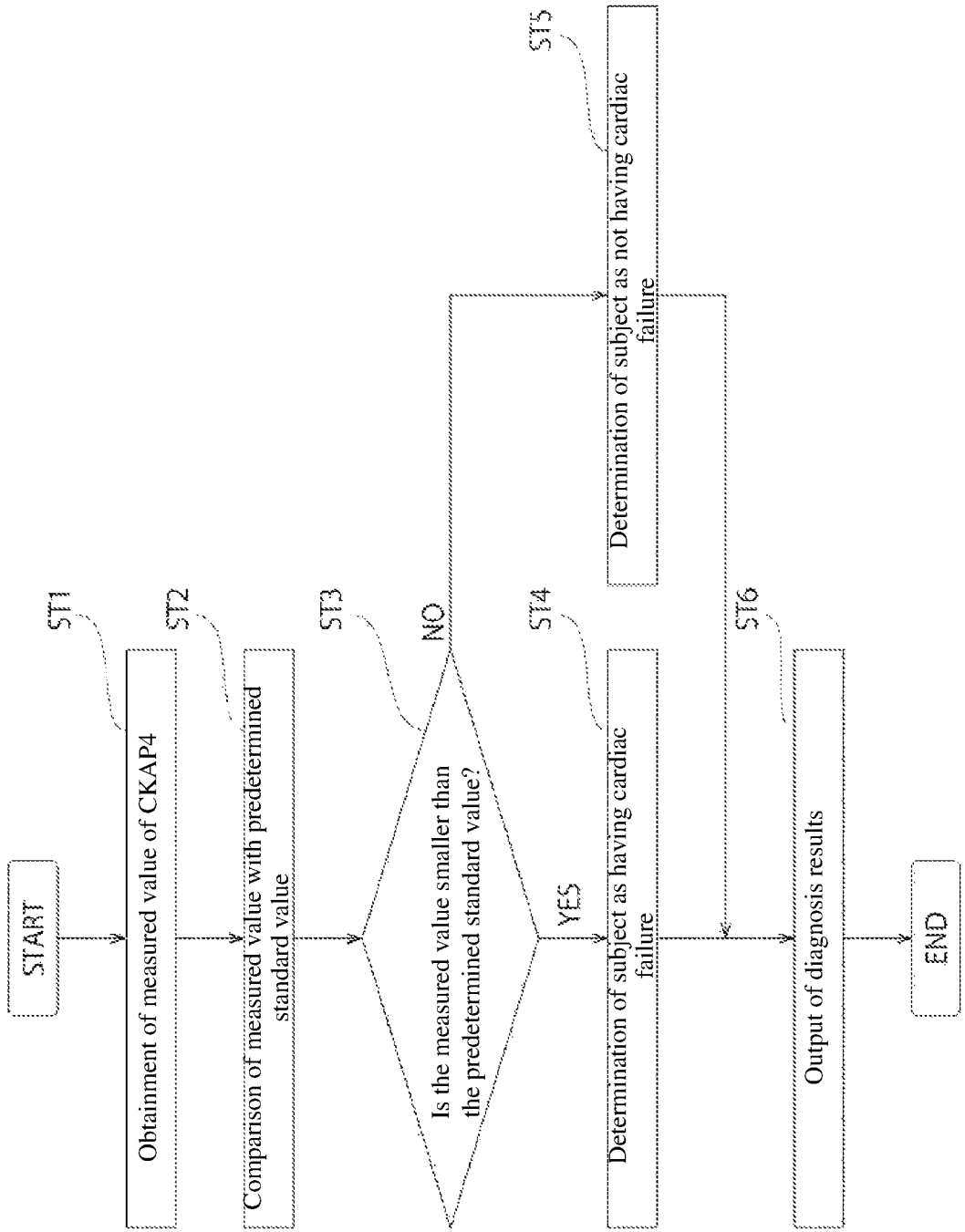
FIG. 13 is a flowchart of a method for detecting a cardiac failure patient using the device for detecting a cardiac failure patient.

Next, with reference to FIG. 13, a detection method of a cardiac failure patient executed by the detection device 1 based on the cardiac failure patient detection program will be described. First, in step ST1, upon receiving the transmission of optical information (signal) from the measuring device 2, the CPU 40 calculates the measured value of CKAP4 in the blood sample from the obtained optical information and stores the measured value in the ROM 41 or the hard disk 43. Then, in step ST2, the CPU 40 compares the obtained measured value of CKAP4 with the predetermined standard value (cutoff value) stored in the ROM 41 or the hard disk 43. When the measured value of CKAP4 is lower than the predetermined standard value (cutoff value), step ST3 proceeds to "YES", leading to ST4 where the CPU 40 determines that the subject from whom the blood sample is collected is a cardiac failure patient. In step ST6, the CPU 40 outputs the determination results, and displays the results on the display part 5 or print the results using a printer. The result that the subject from whom the blood sample is collected is a cardiac failure patient may be stored in the ROM 41 or the hard disk 43. On the other hand, when the measured value of CKAP4 is the same as or higher than the predetermined standard value (cutoff value) (equal to or greater than the predetermined standard value), the step ST3 proceeds to "NO", leading to step ST5, and the CPU 40 determines that the subject from whom the blood sample is collected is not a cardiac failure patient. Then, in the step ST6, the CPU 40 outputs the determination results, and displays the results on the display part 5 or prints the results using a printer. The result that the subject from whom the blood sample is collected is not a cardiac failure patient may be stored in the ROM 41 or in the hard disk 43. In this case, when the subject is a cardiac disease patient or a person suspected of having a cardiac disease, the subject can be determined to be affected with a cardiac disease other than cardiac failure, and the CPU 40 can output the determination results. Thus, in the present embodiment, the present embodiment is also possible to discriminate whether or not a cardiac disease patient or a person suspected of having a cardiac disease is developing cardiac failure.

One embodiment of the detection device for a cardiac failure patient and the detection program for a cardiac failure patient according to the present invention has been described above. However, the present invention is not limited to the embodiment mentioned above, and various modifications may be made without departing from the spirit of the present invention.

7. Method for Treating Cardiac Failure

One embodiment of the present invention provides a method of treating a cardiac failure. The method comprises steps of: obtaining a measured value of CKAP4 in a blood sample collected from a subject; comparing the measured value of CKAP4 with a standard value; and determining the subject as being a cardiac failure patient, which are explained above. The method of treating a cardiac failure further comprises a step of treating a cardiac failure of the subject who is determined to be a cardiac failure patient in the determining step. The treatment may comprises intratracheal intubation, extracorporeal ultrafiltration method (ECUM), continuous hemodiafiltration (CHDF), intra aortic balloon pumping (IABP), percutaneous cardiopulmonary support (PCPS), ventricular assist device (VAS), administration of drugs for cardiac failure and so on. The drugs for cardiac failure comprises vasodilators, diuretic, cardiotonic, antiarrhythmic drug and so on.

EXAMPLES

Hereinafter, the present invention will be described in more detail with reference to Examples, but the present invention is not construed as being limited to the embodiments of Examples.

Example: Measurement of CKAP4 Concentration in Serum

In order to compare CKAP4 concentration in serum of each patient with each disease, CKAP4 concentration in serum of each subject of 6 groups shown in Table 2 were measured.

1. Subject

The details of the subjects are shown in Table 2

TABLE 2

| Group No. | Subject | | Number of subjects |
|---|---|---|---|
| 1 | Cardiac failure patient | Cardiac patients due to ischemic cardiac disease (myocardial infarction) | 15 |
| 2 | | Cardiac failure patients due to dilated cardiomyopathy | 15 |
| 3 | | Hypertension patients | 10 |
| 4 | | Hypertrophic cardiomyopathy patients | 10 |
| 5 | | Atrial fibrillation patients | 10 |
| 6 | | Healthy volunteers | 10 |

Here, the patients in the groups 1 and 2 are patients diagnosed not only as having ischemic cardiac disease or dilated cardiomyopathy as an underlying disease but also as developing cardiac failure, and the patients in the groups 3 to 5 are patients who have an underlying disease but do not develop cardiac failure yet. The healthy volunteers in the group 6 are persons who are not suspected of having any diseases including not only cardiac diseases but also other diseases.

2. Measurement Method

Blood was collected from a subject, and serum separated therefrom was cryopreserved at −80° C. until the measurement.

CKAP4 in the serum was measured according to the attached protocol using an ELISA kit purchased from MyBioSource Inc. (San Francisco, San Diego, USA).

For statistical analysis, one-way analysis of variance was performed using StatFlex, and Turkey test was used for multi-group comparison. For sensitivity and specificity tests, ROC analysis was performed to determine an AUC.

3. Result (1) CKAP4 Concentration in Serum

The mean±standard deviation (pg/ml) of CKAP4 concentration in serum of each group is shown in Table 3.

TABLE 3

| Group No. | CKAP4 concentration in serum (pg/ml) |
|---|---|
| 1 | 342 ± 42* |
| 2 | 393 ± 49* |
| 3 | 742 ± 34 |
| 4 | 639 ± 50 |
| 5 | 726 ± 26 |
| 6 | 773 ± 15 |

The symbol * indicates that a significant difference was $p<0.05$ for the hypertension patient group (group 3), the atrial fibrillation patient group (group 4), the hypertrophic cardiomyopathy patient group (group 5), and the healthy volunteer group (group 6).

From the above results, it was revealed that the CKAP4 concentrations in sera of the cardiac failure patients due to ischemic cardiac diseases of the group 1 and the cardiac failure patients due to dilated cardiomyopathy of the group 2 were lower than the CKAP4 concentrations of the healthy volunteers. In addition, it was clear that the CKAP4 concentrations in sera did not change in the patients with hypertension, atrial fibrillation or hypertrophic cardiomyopathy.

The results suggested that the concentration of CKAP4 in a blood sample from a patient who had developed cardiac failure was lower than that in a blood sample from each of other cardiac disease patients or healthy volunteers.

(2) ROC Analysis (Receiver Operating Characteristic Analysis)

In order to evaluate whether or not CKAP4 concentration in serum is specific for cardiac failure, ROC analysis was performed. The AUC values obtained by ROC analysis are shown in Table 4. The closer the AUC value is to 1.0, the higher the specificity is. Also, the ROC curves of the groups are shown in FIGS. 2 to 9.

TABLE 4

|  | Versus Group 6 | Versus Group 3 | Versus Group 4 | Versus Group 5 |
|---|---|---|---|---|
| Group 1 | 1.0 | 0.99 | 0.93 | 0.93 |
| Group 2 | 0.96 | 0.91 | 0.84 | 0.93 |

The cardiac failure patient group (group 1) due to ischemic cardiac disease showed a higher AUC value than the healthy volunteer group (group 6), and the measurement of the CKAP4 concentration in the blood was shown to be very effective in detecting the presence or absence of cardiac failure due to ischemic cardiac disease. In addition, the AUC value for the hypertensive patient group (group 3), the hypertrophic cardiomyopathy patient group (group 4), and the atrial fibrillation patient group (group 5) was shown to be high, indicating that this was effective in discrimination diagnosis of these diseases from cardiac failure due to ischemic cardiac disease.

The cardiac failure patient group (group 2) due to dilated cardiomyopathy also showed a higher AUC value than the healthy volunteer group (group 6), and the measurement of the CKAP4 concentration in the blood sample was shown to be very effective in detecting the presence or absence of cardiac failure due to dilated cardiomyopathy. In addition, the AUC value for the hypertensive patient group (group 3), the hypertrophic cardiomyopathy patient group (group 4), and the atrial fibrillation patient group (group 5) was also shown to be high, indicating that this was effective in discrimination diagnosis of these diseases from cardiac failure due to dilated cardiomyopathy.

From this analysis, the decrease in the CKAP4 concentration in the blood sample was considered to be specific to cardiac failure.

REFERENCE SIGNS LIST

1: Detection device
2: Measuring device
3: Computer system
4: Computer
40: Processor (CPU)
41: ROM
42: RAM
43: Hard disk (HDD)
50: Test kit
55: Exterior box
51: First container
52: Second container
53: Third container
54: Package insert
55: Exterior box

The invention claimed is:

1. A method for treating a patient determined to be in cardiac failure resulting from dilated cardiomyopathy or ischemic cardiac disease, said method comprising the steps of:
  (1) measuring the amount of Cytoskeleton-associated protein 4 (CKAP4) in a blood sample collected from one or more subjects with dilated cardiomyopathy or ischemic cardiac disease;
  (2) selecting a subject, from said one or more subjects, as a subject in cardiac failure when the measured amount of CKAP4 in the blood sample from the subject is lower than the amount of CKAP4 in a blood sample from a healthy individual; and
  (3) performing at least one treatment for cardiac failure on said selected patient, wherein said treatment is selected from the group consisting of intratracheal intubation, extracorporeal ultrafiltration method (ECUM), continuous hemodiafiltration (CHDF), intra aortic balloon pumping (IABP), percutaneous cardiopulmonary support (PCPS), ventricular assist device (VAS), and administration of an effective amount of a drug for treating cardiac failure.

2. The method according to claim 1, wherein the measuring step comprises:
  bringing the blood sample into contact with an anti-CKAP4 antibody;
  forming a complex containing CKAP4 in the blood sample and the anti-CKAP4 antibody; and
  measuring CKAP4 by detecting the complex.

3. The method according to claim 1, wherein the measuring step comprises:
  bringing the blood sample, a solid phase, a first anti-CKAP4 antibody, a second anti-CKAP4 antibody, and a labeling substance into contact with one another;
  forming, on the solid phase, a complex containing CKAP4 in the blood sample, the first anti-CKAP4 antibody, the second anti-CKAP4 antibody, and the labeling substance; and
  measuring CKAP4 by detecting the complex.

4. The method according to claim 3, wherein after formation of the complex, the solid phase is washed to remove a component not forming the complex.

5. The method according to claim 1, wherein the drug for treating cardiac failure is selected from the group consisting of a vasodilator, a diuretic, a cardiotonic, and an antiarrhythmic drug.

* * * * *

SEQUENCE LISTING

```
<160> NUMBER OF SEQ ID NOS: 1

<210> SEQ ID NO 1
<211> LENGTH: 602
<212> TYPE: PRT
<213> ORGANISM: Homo sapiens

<400> SEQUENCE: 1

Met Pro Ser Ala Lys Gln Arg Gly Ser Lys Gly Gly His Gly Ala Ala
1               5                   10                  15

Ser Pro Ser Glu Lys Gly Ala His Pro Ser Gly Gly Ala Asp Asp Val
            20                  25                  30

Ala Lys Lys Pro Pro Pro Ala Pro Gln Gln Pro Pro Pro Pro Pro Ala
        35                  40                  45

Pro His Pro Gln Gln His Pro Gln Gln His Pro Gln Asn Gln Ala His
    50                  55                  60

Gly Lys Gly Gly His Arg Gly Gly Gly Gly Gly Gly Lys Ser Ser
65                  70                  75                  80

Ser Ser Ser Ser Ala Ser Ala Ala Ala Ala Ala Ala Ser Ser
                85                  90                  95

Ser Ala Ser Cys Ser Arg Arg Leu Gly Arg Ala Leu Asn Phe Leu Phe
            100                 105                 110

Tyr Leu Ala Leu Val Ala Ala Ala Ala Phe Ser Gly Trp Cys Val His
        115                 120                 125

His Val Leu Glu Glu Val Gln Gln Val Arg Arg Ser His Gln Asp Phe
    130                 135                 140

Ser Arg Gln Arg Glu Glu Leu Gly Gln Gly Leu Gln Gly Val Glu Gln
```

-continued

```
            145                 150                 155                 160
            Lys Val Gln Ser Leu Gln Ala Thr Phe Gly Thr Phe Glu Ser Ile Leu
                            165                 170                 175
            Arg Ser Ser Gln His Lys Gln Asp Leu Thr Glu Lys Ala Val Lys Gln
                            180                 185                 190
            Gly Glu Ser Glu Val Ser Arg Ile Ser Glu Val Leu Gln Lys Leu Gln
                            195                 200                 205
            Asn Glu Ile Leu Lys Asp Leu Ser Asp Gly Ile His Val Val Lys Asp
                210                 215                 220
            Ala Arg Glu Arg Asp Phe Thr Ser Leu Glu Asn Thr Val Glu Glu Arg
            225                 230                 235                 240
            Leu Thr Glu Leu Thr Lys Ser Ile Asn Asp Asn Ile Ala Ile Phe Thr
                            245                 250                 255
            Glu Val Gln Lys Arg Ser Gln Lys Glu Ile Asn Asp Met Lys Ala Lys
                            260                 265                 270
            Val Ala Ser Leu Glu Glu Ser Glu Gly Asn Lys Gln Asp Leu Lys Ala
                            275                 280                 285
            Leu Lys Glu Ala Val Lys Glu Ile Gln Thr Ser Ala Lys Ser Arg Glu
                290                 295                 300
            Trp Asp Met Glu Ala Leu Arg Ser Thr Leu Gln Thr Met Glu Ser Asp
            305                 310                 315                 320
            Ile Tyr Thr Glu Val Arg Glu Leu Val Ser Leu Lys Gln Glu Gln Gln
                            325                 330                 335
            Ala Phe Lys Glu Ala Ala Asp Thr Glu Arg Leu Ala Leu Gln Ala Leu
                            340                 345                 350
            Thr Glu Lys Leu Leu Arg Ser Glu Glu Ser Val Ser Arg Leu Pro Glu
                            355                 360                 365
            Glu Ile Arg Arg Leu Glu Glu Leu Arg Gln Leu Lys Ser Asp Ser
                370                 375                 380
            His Gly Pro Lys Glu Asp Gly Gly Phe Arg His Ser Glu Ala Phe Glu
            385                 390                 395                 400
            Ala Leu Gln Gln Lys Ser Gln Gly Leu Asp Ser Arg Leu Gln His Val
                            405                 410                 415
            Glu Asp Gly Val Leu Ser Met Gln Val Ala Ser Ala Arg Gln Thr Glu
                            420                 425                 430
            Ser Leu Glu Ser Leu Leu Ser Lys Ser Gln Glu His Glu Gln Arg Leu
                            435                 440                 445
            Ala Ala Leu Gln Gly Arg Leu Glu Gly Leu Gly Ser Ser Glu Ala Asp
                450                 455                 460
            Gln Asp Gly Leu Ala Ser Thr Val Arg Ser Leu Gly Glu Thr Gln Leu
            465                 470                 475                 480
            Val Leu Tyr Gly Asp Val Glu Glu Leu Lys Arg Ser Val Gly Glu Leu
                            485                 490                 495
            Pro Ser Thr Val Glu Ser Leu Gln Lys Val Gln Glu Gln Val His Thr
                            500                 505                 510
            Leu Leu Ser Gln Asp Gln Ala Gln Ala Ala Arg Leu Pro Pro Gln Asp
                            515                 520                 525
            Phe Leu Asp Arg Leu Ser Ser Leu Asp Asn Leu Lys Ala Ser Val Ser
                530                 535                 540
            Gln Val Glu Ala Asp Leu Lys Met Leu Arg Thr Ala Val Asp Ser Leu
            545                 550                 555                 560
            Val Ala Tyr Ser Val Lys Ile Glu Thr Asn Glu Asn Asn Leu Glu Ser
                            565                 570                 575
```

```
Ala Lys Gly Leu Leu Asp Asp Leu Arg Asn Asp Leu Asp Arg Leu Phe
            580                 585                 590
Val Lys Val Glu Lys Ile His Glu Lys Val
            595                 600
```